United States Patent [19]

Wohltjen et al.

[11] Patent Number: 5,550,062
[45] Date of Patent: Aug. 27, 1996

[54] METHOD AND APPARATUS FOR CHEMICAL DETECTION BY PYROLYSIS

[75] Inventors: Henry Wohltjen, Bowling Green, Ky.; Edward J. Poziomek, Las Vegas, Nev.

[73] Assignee: Microsensor Systems, Inc., Bowling Green, Ky.

[21] Appl. No.: 144,876

[22] Filed: Oct. 27, 1993

[51] Int. Cl.$^6$ .................................. G01N 21/72
[52] U.S. Cl. .................. 436/155; 436/92; 436/901
[58] Field of Search .................... 422/80; 436/92, 436/155, 901

[56] References Cited

U.S. PATENT DOCUMENTS

| | | | |
|---|---|---|---|
| 4,312,228 | 1/1982 | Wohltjen | 73/597 |
| 4,759,210 | 7/1988 | Wohltjen | 73/23 |
| 5,110,747 | 5/1992 | Pataschnick et al. | 436/133 |

OTHER PUBLICATIONS

Abstract entitled "Chemical Microsensor Arrays for the Passive Detection of Chemical Vapors for Counter Drug Application–Detection of Illicit Drugs Through Analysis of Prolysis Products with SAW Microsensor Array".

Wohltjen et al., "Chemical Vapor SAW Microsensor Array for Application in Drug Interdiction: Instrument Design and Developement," *Proc. of Int'l Symp. on Substance Identification Technologies,* Innsbruck, Austria (submitted for publication).

Wohltjen and Dessey, "Surface Acoustic Wave Probe for Chemical Analysis, I. Introduction and Instrument Design," *Anal. Chem.,* 51(9): 1458–1464 (1979).

Wohltjen, "Mechanism of Operation and Design Consideration for Surface Acoustic Wave Vapor Sensors," *Sensors and Actuators,* 5(4):307–325 (1984).

Poziomek et al., "Chemical Markers for the Detection and Identification of Cocaine and Cocaine Hydrochloride" (presented in the Contraband and Cargo Inspection Technology International Symposium, Washington, D.C. on Oct. 28, 1992).

*Primary Examiner*—David A. Redding
*Attorney, Agent, or Firm*—Curtis, Morris, & Safford, P.C.

[57] ABSTRACT

This invention relates to a method and apparatus for detecting and identifying a non-volatile chemical substance, in which the chemical substance (when in a sample) is pyrolyzed into its gaseous components and then the gaseous components are monitored to determine whether or not specific gaseous components are present.

15 Claims, 6 Drawing Sheets

METHOD AND APPARATUS FOR CHEMICAL DETECTION BY PYROLYSIS

FIELD OF THE INVENTION

The present invention relates to a new method and apparatus for determining whether a non-volatile chemical substance is present in a sample of interest utilizing a controlled pyrolysis. More particularly, this invention relates to a method and apparatus which enable the detection and identification of various gaseous products resulting from the pyrolysis of the chemical substance of interest such that, when the gaseous products are present, the chemical substance's material presence is also confirmed. Correspondingly, when those products are absent the substance is confirmed not to be present in any material amount.

BACKGROUND OF THE INVENTION

There are many chemical agents that need to be detected and monitored that are not conveniently handled by conventional chemical detection apparatti such as chromatographs or spectrometers. Especially inconvenient are chemicals that are solids at room temperature since they must often be dissolved in a solvent before an analysis can be performed. Analytical chemistry techniques are not helpful with these agents because they require skill, often lack great sensitivity or selectivity, and are not well suited for incorporation into portable, direct-reading instruments.

A typical example of such agents is the illicit drug cocaine hydrochloride. This material has an extremely low vapor pressure which makes it nearly impossible to detect as a vapor with popular vapor sniffers such as ion mobility spectrometers, gas chromatographs, electrochemical sensors, etc. Thus, when searching for cocaine hydrochloride, the drug will only be found as minute particles, or possibly as an adsorbate on ambient aerosol particles.

One possibility that shows great potential for monitoring ambient air for the presence of chemical vapors of interest is microsensor technology. See H. Wohltjen et al., "Chemical Vapor SAW Microsensor Array for Application in Drug Interdiction: Instrument Design and Development", Proc of Int'l Symp. on Substance Identification Technologies, Innsbruck, Australia (Oct. 4, 1993). The use of chemical microsensors to monitor gas has been the subject of U.S. Pat. No. 4,759,210, granted Jul. 26, 1988, to Microsensor Systems, Inc., the subject matter of which is incorporated herein by reference.

Chemical microsensors are generally defined as solid state, micro-fabricated electronic structures that respond to their chemical environment. They include a variety of devices, such as surface acoustic wave (SAW) devices, organic and inorganic semiconductors, ChemFETs, microelectrode arrays for electrochemical measurements, and other electronic structures. Even though each type of microsensor may respond in a different way to a chemical environment, they share many desirable features. For example, they are all very small, sensitive, rugged, relatively inexpensive, low maintenance, and provide an electrical signal that can be readily integrated into a measurement system.

One class of chemical microsensor, the surface acoustic wave ("SAW") device, has received increasing attention in the research and development community, and is being incorporated into many prototype chemical monitors for introduction to the field. SAW devices were first proposed as sensors for chemical vapors in 1979. H. Wohltjen and R. E. Dessy, "Surface Acoustic Wave Probe for Chemical Analysis, I. Introduction and Instrument Design", *Anal. Chem.*, 51 (9): 1458–1464 (1979). Since then many studies have been undertaken to improve their sensitivity by increasing operating frequency or by improving device configuration, such as operating the SAW devices in the resonant mode rather than as delay lines. The selectivity of SAW devices for specific chemicals has also been improved over the years through the development of better surface coatings and the use of SAW sensors in multiple sensor arrays (with each SAW device having a different chemically sensitive coating). This array of sensors can be coupled to a pattern recognition processor to enhance the operational selectivity of the sensor system. These pattern recognition processor systems employ a pattern recognition algorithm to analyze data fed to the processor from the array of sensors when those sensors come in contact with chemical species which it is desired to detect. See H. Wohltjen, "Mechanism of Operation and Design Considerations for Surface Acoustic Wave Vapor Sensors," *Sensors and Actuators*, 5(4):307–325 (1984).

SAW microsensors and SAW microsensor arrays have most recently been incorporated into a number of novel applications, i.e. chemical warfare (CW) agent detectors. One of these CW agent detectors was a "Smart Sensor" SAW array system built for the Air Force. It utilized four SAW devices, each with a different chemically sensitive coating. The combination of the four SAW sensors with pattern recognition proved to be very sensitive and selective for various chemical warfare agents with effective discrimination against anticipated interfering vapors. The sensitivity of detecting and identifying some agents were as low as 0.01 $mg/m^3$ in a two minute analysis. Even lower detection limits were possible using longer sample concentration times. Above their threshold detection limits, each CW agent could be identified 100% of the time, even when present in mixtures with other vapors at concentrations that were 50 times higher than the agent.

However, while the aforementioned technology is quite beneficial, it does not work effectively with non-volatile substances. This has frustrated that technology's application to the investigation of samples of interest for such non-volatile substances, and particularly for illicit substances of that sort such as cocaine hydrochloride and heroin. Thus, the art has not taken appropriate advantage of this powerful analytical tool.

The development of a convenient and accurate method and apparatus for investigating samples of interest to determine whether they contain non-volatile analytes would be a significant step forward in the art.

OBJECTS OF THE INVENTION

It is an object of the invention to provide a method and apparatus for determining whether a non-volatile chemical substance is present in a sample of interest.

It is another object of the invention to provide a method and apparatus suitable for pyrolyzing a chemical substance of interest, when present in a sample, to form one or more gaseous pyrolysis products and then monitoring to determine whether or not such gaseous pyrolysis products are present.

It is yet another object of the present invention to provide a method and apparatus with a high degree of selectivity in respect of gaseous products resulting from the pyrolysis of a non-volatile chemical substance.

It is yet another object of the present invention to provide a method and apparatus capable of detecting very small amounts of gaseous products resulting from the pyrolysis of a non-volatile chemical.

It is still another object of the present invention to provide a method and apparatus which concentrate certain gas species resulting from pyrolysis of a non-volatile chemical substance, when present in a sample to be analyzed, to a high degree.

It is a further object of the present invention to provide a method and apparatus which are highly effective in the detection and identification of gaseous products resulting from pyrolysis of a non-volatile chemical substance, by providing an increased amount of chemical information about one or more gaseous products being monitored, especially when detection and identification of the gaseous products is carried out with the use of pattern recognition techniques.

STATEMENT AND ADVANTAGES OF THE INVENTION

In one of its aspects, the present invention relates to a method for determining the amount of a non-volatile chemical substance of interest present in a sample, which comprises the steps of: (a) introducing said sample into a pyrolysis zone; (b) subjecting said sample to an elevated temperature less than 300° C. such that any of said chemical substance of interest present in the sample is pyrolyzed to yield a pyrolysis product; (c) extracting an amount of gaseous material resident in said pyrolysis zone, and introducing said amount of gaseous material into a detection zone where it is contacted with a sensing apparatus which selectively senses the presence of a product of the pyrolysis of said chemical substance and produces a signal representative of the results of such sensing; and (d) analyzing the signal produced due to sensing of said amount of gaseous material as an indication of the amount of said chemical substance of interest present in the sample.

In another aspect, the invention relates to apparatus for determining the amount of a non-volatile chemical substance of interest present in a sample, which comprises pyrolysis means for subjecting said sample to elevated temperature to pyrolyze said chemical substance when present and, associated therewith, means for defining a pyrolysis chamber in which said pyrolysis means resides; detection means for selectively sensing the presence of one or more products of the pyrolysis of said chemical substance and for producing a signal representative of the results of said sensing, and, associated therewith, means for defining a detection chamber in which the detection means resides; extraction means for drawing gaseous material from said pyrolysis chamber and introducing said material into said detection chamber; analysis means for evaluating the signal produced due to sensing of a said amount of gaseous material as an indication of the amount of said chemical substance of interest; and control means for (a) causing said pyrolysis means to subject said sample, when it is in the pyrolysis chamber, to a temperature of less than 300° C. such that any of said chemical substance contained therein is pyrolyzed, (b) causing said extraction means to draw from the pyrolysis chamber said amount of gaseous material, and to introduce such amount into the detection chamber, (c) causing said detection means to sense selectively the amount of said pyrolysis product present in said amount of gaseous material and produce a signal representative of the results of such sensing, and (d) causing said analysis means to evaluate the signal produced due to sensing of said amount of gaseous material as an indication of the amount of the chemical substance present.

As evident from the foregoing, substantial advantages accrue with the practice of the present invention.

The present invention is useful in detecting gaseous pyrolysis products of a non-volatile chemical substance after the substance has been pyrolyzed, to determine whether or not the substance is present in a sample to be analyzed, as well as for the purpose of detecting and identifying various constituents of a gas to be monitored. Illicit drugs such as cocaine hydrochloride and heroin—which have negligible vapor pressures and are difficult to detect with conventional microsensor techniques—produce very characteristic chemical vapors when pyrolyzed. The pyrolysis can occur at relatively low temperatures, easily obtained in a small, portable instrument. Accordingly, the invention is well suited for use in applications involving drug interdiction.

Also, heating of a non-volatile chemical substance to obtain its gaseous pyrolysis products provides a fast and convenient means for determining its identity not otherwise available with conventional wet chemistry techniques. The direct provision of the gaseous products to the sensing means enables prompt and full contact of the gaseous products therewith.

Further, with practice of the invention one achieves a high yield of gaseous products for analysis through pyrolyzing the non-volatile chemical substance, and a high degree of collection efficiency of the gaseous pyrolysis products. This leads to a particularly accurate and sensitive determination of the amount of such products and, therefore, the non-volatile chemical substance itself.

Moreover, because it utilizes microsensor technology, the invention is adaptable to miniaturization, with concomitant savings in cost to operate and in convenience of use in space-limited applications or in applications requiring portability.

The present invention, including further objectives, features and advantages thereof, will be more fully understood from the following description of certain preferred embodiments, when read with reference to the accompany drawings.

DESCRIPTION OF CERTAIN PREFERRED EMBODIMENTS

Figure 1:
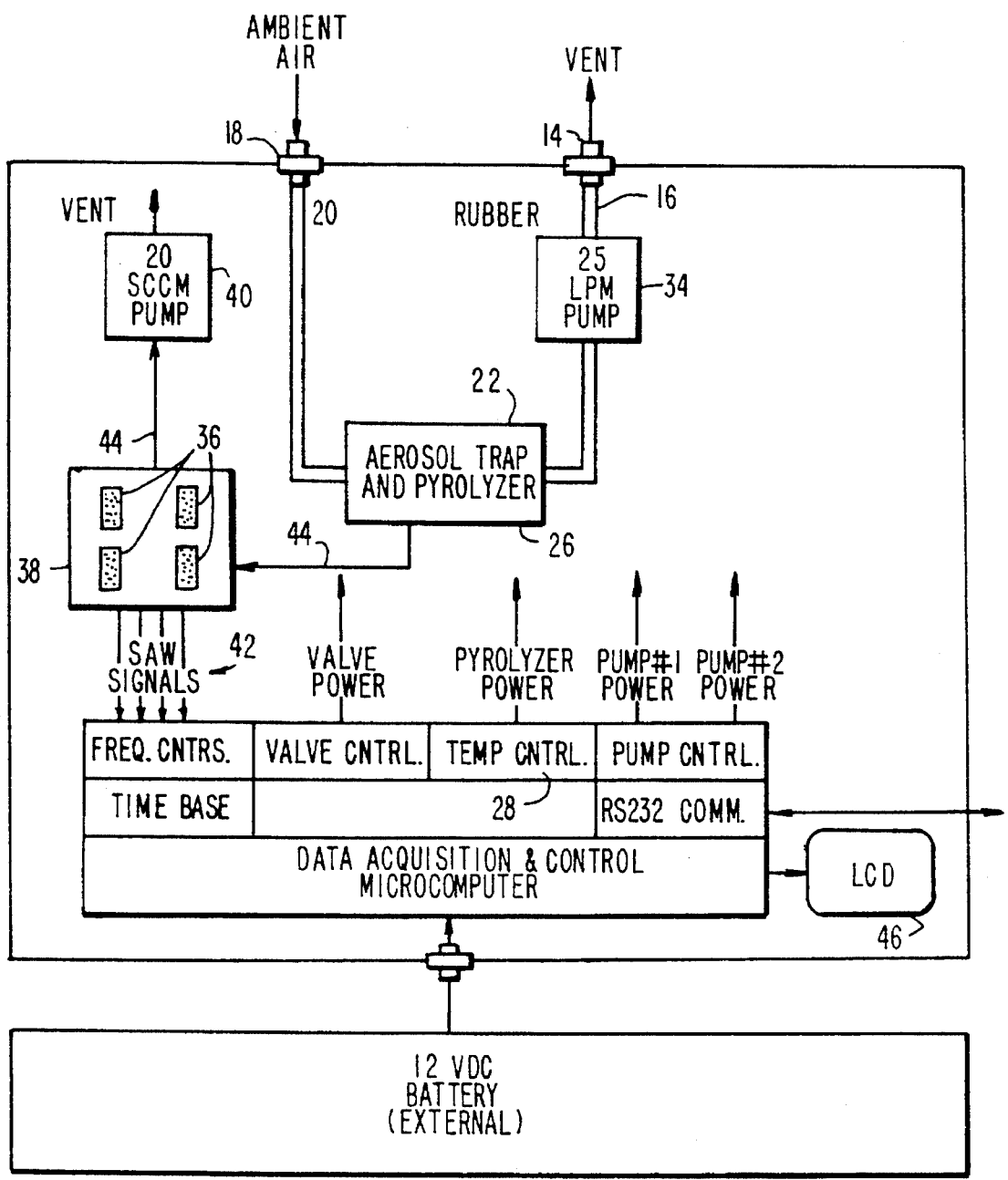
FIG. 1 is a block diagram of apparatus for pyrolyzing a chemical substance (when present in a sample) into gaseous products, and then detecting and identifying any gaseous pyrolysis products of such substance which may be present in the gas to be monitored.

Generally, three steps are required in the operation of the invention. First, a sample is collected using a pump to pull a large volume of air over a trap that will retain small particles. Second, the trapping filter is heated to a predetermined temperature, whereupon the non-volatile chemical substance of interest is made to decompose into characteristic decomposition product molecules that are in the vapor state. Third, these vapor phase pyrolysis products are detected and identified using a suitable sensor.

The present invention involves the collection of samples such as dust and aerosols, which could potentially contain the non-volatile chemical substance of interest, on or in a trap of suitable composition and configuration to separate and concentrate them for further analysis. For example, the sample is drawn into the trap by a high-flow-rate air pump. This can be the pumping arrangement from a small powerful vacuum cleaner (such as the type commercially branded DUST BUSTER (trademark)) or any other suitably sized and powered pump apparatus which is capable of drawing the dust, aerosol or other sample into contact with the trap. The trap is advantageously a glass wool (e.g., a bed), porous teflon (e.g., a filter), porous glass fiber (e.g., a filter) or other suitable substance. The trap is advantageously configured so as to maximize contact between it and the sample to be analyzed for the purpose of trapping the sample as effectively and in as short an amount of time as possible.

Once the sample (e.g., dust and/or aerosol particles) is concentrated in the trap, it is subjected to pyrolysis conditions. This is carried out in the pyrolysis chamber or zone where the pyrolyzer unit heats the trapped sample to a predetermined temperature effective to vaporize the chemical substance, when present, to gaseous products. The pyrolysate are then transferred to the SAW sensors, which are monitored for response to the characteristic vapors.

The pyrolyzing equipment can be of any type suitable for vaporizing the non-volatile chemical substance of interest, but preferably comprises a resistance heater. The pyrolysis equipment need only be capable of pyrolyzing the chemical substances at a temperature up to about 300° C., but should advantageously be sensitive to adjustment of the temperature within that range in order to achieve good control over these operations.

After pyrolysis, any gaseous products thereof are passed to the sensing equipment. The sensing equipment is advantageously an array of sensing components arranged for contact with the gaseous products to be monitored. The sensing means advantageously comprise chemical sensors which, in and of themselves, are known to those of ordinary skill in the art. Illustratively, the means for sensing gaseous material is a piezoelectric sensor, an organic chemiresistor, a chemically sensitive field effect transistor, a metal oxide semiconductor, or an electrochemical cell. As piezoelectric sensors it is suitable to employ, for instance, a bulk wave piezoelectric sensing device or a surface wave sensor device as described in Wohltjen U.S. Pat. No. 4,312,228, granted Jan. 26, 1982. The subject matter of the patent is incorporated by reference herein.

In several especially advantageous embodiments of the invention, the portion of the sensor which directly interacts with the gaseous products of interest is made from the sorbent coating applied to a bulk wave piezoelectric sensing device or a SAW device.

The sensing components thus bear a sorbent coating disposed such that it intercepts the gas transferred to such means. A plurality of the sensing components is typically arranged in an array so that the gaseous products flow by each simultaneously. However, in other embodiments it is more preferable to arrange the sensing components in series so that the gaseous products encounter the sensor units sequentially. Alternative configuration are suitable as long as the arrangement of the devices permits flow of the gas therethrough in accordance with the practice of the invention as herein described. Once equipped with the teachings herein, one of ordinary skill in the art will be capable of selecting an appropriate arrangement of sensor components.

The sorbent coating is any suitable material which is selective to sorption of a gaseous pyrolysis product consistent with the practice of the present invention. Such sorbent coatings, in and of themselves, are well known in the art. Examples of sorbent coatings which are suitable for practice of the present invention are activated charcoal, alumina, zeolite molecular sieves, metals such as transition metals and especially metals of group Ib and group VIII of the periodic table, silica gel and polymeric sorbents. There are many suitable polymeric sorbent coatings which are well-known to those of ordinary skill in the art for use in connection with, for example, gas-chromatographic techniques. Illustratively, sorbent coatings which are well-known to those of ordinary skill in the art are used in connection with, for example, gas-chromatographic techniques.

The sorbent coatings placed in each of the sensing components is advantageously chosen so that its selectivity to sorption of gaseous pyrolysis products to be monitored is different from that of sorbent used in each of the other sensor devices utilized. The selectivity characteristics of the various sorbent coating which can be utilized in accordance with the invention are generally well-known in the art. In any case, these characteristics can be determined empirically by the practitioner of the invention without undue experimentation and through the exercise of routine skill of the art, especially in light of the predetermination of gaseous species which the practitioner seeks to detect or anticipates may be present in the gaseous products to be monitored.

The sorbent coating is generally employed in an amount sufficient so as to effect a degree of concentration of the gaseous product to which the sorbent is selective (should such gaseous product be present) which will permit detection and identification. Determination of the amount of sorbent to be used may involve taking into account the magnitude of the sampling period, i.e., the time period during which the gaseous products are in contact with the device in connection with the sensing operation. Other factors which will be apparent to one of ordinary skill in the art, such as the amount of gaseous products contacting the device, can also have an effect on the amount of sorbent which is advantageously utilized. These factors will be readily determinable by one of ordinary skill in the art equipped with the knowledge of the invention which can be derived herefrom, and taking into account the amount of gaseous pyrolysis product(s) reasonably likely to be released (in the event the substance of interest is present) judging by the sample size.

Ordinarily, during contact of any gaseous products with the trapping means, conditions are maintained such that the sorbent coating can sorb (either adsorb or absorb) one or more gas products of interest should such species be present. Normally, this operation would be carried out at room temperature and pressure, but other conditions under which gaseous products if present can be sorbed are also suitable (although this may cause some change in collection efficiency).

The sensors of the claimed invention are typically components which emit a change in output signal when they come in contact with gaseous material to be contacted in accordance with the invention. Thus, a change in chemical concentration or activity occurs at the portion of a sensor when it is exposed to the aforementioned gaseous species. This results in a change in current, frequency, voltage or some other measurable parameter and generation of a corresponding signal indicating the presence of the gaseous product. Contact with a plurality of sensing means utilized in accordance with certain embodiments of the invention yields a set of signals which can be used as a means of chemically analyzing the gaseous pyrolysis products with which the sensors have come in contact. The set of signal outputs of the sensors forms a "spectrum" of information which is the basis for interpretation and analysis to detect and identify gaseous species which may be present.

The signal from each of the sensing components is relayed to an appropriate processing system for the aforementioned interpretation and analysis to determine whether or not any of the gaseous pyrolysis products to which the sensors are selective is present, and if so to detect that presence and identify the gaseous product(s).

The invention as previously described has as one of its principal and further advantages the ability to compensate for drift which is frequently exhibited by chemical sensors typically used to detect and identify the gaseous material generally of interest in these materials. Drift is a change in the output signal from the sensing means resulting from the effects of temperature, pressure or other in controlled influences over a relatively long period of time. The problem of drift is somewhat endemic to the use of systems in which sensors are utilized to obtain chemical information about a gas to be monitored. The drift, or change in output signals, of those sensors over a relatively long period of time is significant if the detection and identification of chemical or gaseous species requires employment of signal outputs taken on a relatively long-term basis, since a component of any change in the signal can be due to detection of gaseous material to which the sensor is selective. This introduces inaccuracy. However, with the present invention sensor drift can be compensated without sacrificing the advantages of the invention. This is because the present invention is readily adapted to a mode in which the signal from the sensing means can be measured at a time before pyrolysis, thereby to obtain a base signal corresponding to the absence of any gas products to be detected and identified. Then, after pyrolysis, another measurement of the output signal of the sensing means can be obtained before a sufficient amount of time has passed for the drift phenomenon to have introduce an extraneous change in the signal relative to the base signal. The time difference between measurement of the base signal and measurement of the output signal corresponding to passage of the gas containing any gaseous pyrolysis products is insignificant compared to the time required for the output signal of the sensing components to be affected by the drift. By continually measuring the difference between a fresh base signal and a signal obtained shortly thereafter corresponding to sensor-contact with gas containing any gaseous pyrolysis product of interest, any change in signal due to a drift phenomenon over a long period of time is canceled out, thus compensating for the drift and removing any inaccuracy which might otherwise be introduced by comparison of the signals which are no longer normalized.

Accordingly, in certain particularly preferred embodiments, the method further comprises the steps of (i) extracting, before pyrolysis a first amount of atmospheric gaseous material from said zone; and (ii) introducing said first amount into a detection zone, where said first amount is contacted with a sensing apparatus which selectively senses the presence of a product of the pyrolysis of said chemical substance and produces a signal representative of the results of such sensing.

Correspondingly, in certain particularly preferred apparatus embodiments, the analysis means comprises comparator means for comparing the respective signals produced due to sensing of a first amount of said atmospheric gaseous material prior to subjecting said sample to elevated temperature and a second amount of said atmospheric gaseous material, containing a gaseous product of said pyrolysis when the chemical substance is present, as an indication of the amount of said chemical substance of interest; and said control means (i) prior to subjecting said sample to elevated temperature, causes said extraction means to draw from said pyrolysis chamber a first amount of said atmospheric gaseous material, and to introduce such material into the detection chamber, (ii) causes said detection means to sense selectively the amount of said pyrolysis product present in the first amount of said material and produce a signal representative of the results of such sensing; and (iii) causes said comparator means to compare the signals produced due to sensing of said amounts of said atmospheric gaseous material extracted before and after pyrolysis, respectively, as an indication of the amount of the chemical substance present.

Yet another way to prevent drift, and to improve low vapor transfer efficiency resulting from adsorption (i.e., crystallization) on the walls of the detection chamber is to keep the detection chamber at an elevated temperature. The raised temperature in the chamber will lower the clear-down time associated with the chamber after exposure to the sample vapor. Moreover, the drift phenomenon can be minimized since the clear-down time is correspondingly lowered.

One of the principal and essential features of the present invention is that the output from pyrolysis is contacted with each and every one of the sensing units utilized. This produces a spectrum of signals for interpretation based on signals from all the sensors. The amount of chemical information about constituents of the gas being monitored is dramatically increased by using this arrangement.

In connection with the foregoing, a particularly advantageous processing system with which to use the invention is a computerized pattern recognition processor. This type of processor is based on the utilization of a pattern recognition algorithm, the accuracy and reliability of which in analyzing the output of the signals of the associated sensors is substantially increased with an increase in the amount of chemical information (e.g., the number and information content of the spectra) received from each sensor. As discussed above, practice of the present invention increases the amount of chemical information which is yielded by the sensing equipment. Thus, use of the present invention in conjunction with pattern recognition techniques confers a high degree of accuracy and reliability in the detection and identification of any gaseous pyrolysis products of interest in the gas being monitored, without sacrificing other advantages over alternative systems as discussed previously.

The use of a plurality of sensing means enables the invention's practitioner to achieve a large increase in the amount of chemical information outputted by the sensing means. This is particularly important when modern computerized pattern recognition techniques are employed to process and analyze the signals provided by the sensing means, since an increase in selectivity to the various gaseous species of interest and hence the reliability and accuracy of the detection and identification of gaseous species of interest can be improved by providing an increased amount of chemical information from the plurality of sensing means. However, those increases are not obtained at the expense of sacrificing the invention's operational advantages (such as flexibility and relative quickness) in determining what (if any) gaseous pyrolysis products of interest are present, along with their identification, as would contrastingly be the case when using the gas chromatographic techniques described previously herein.

Figure 2:
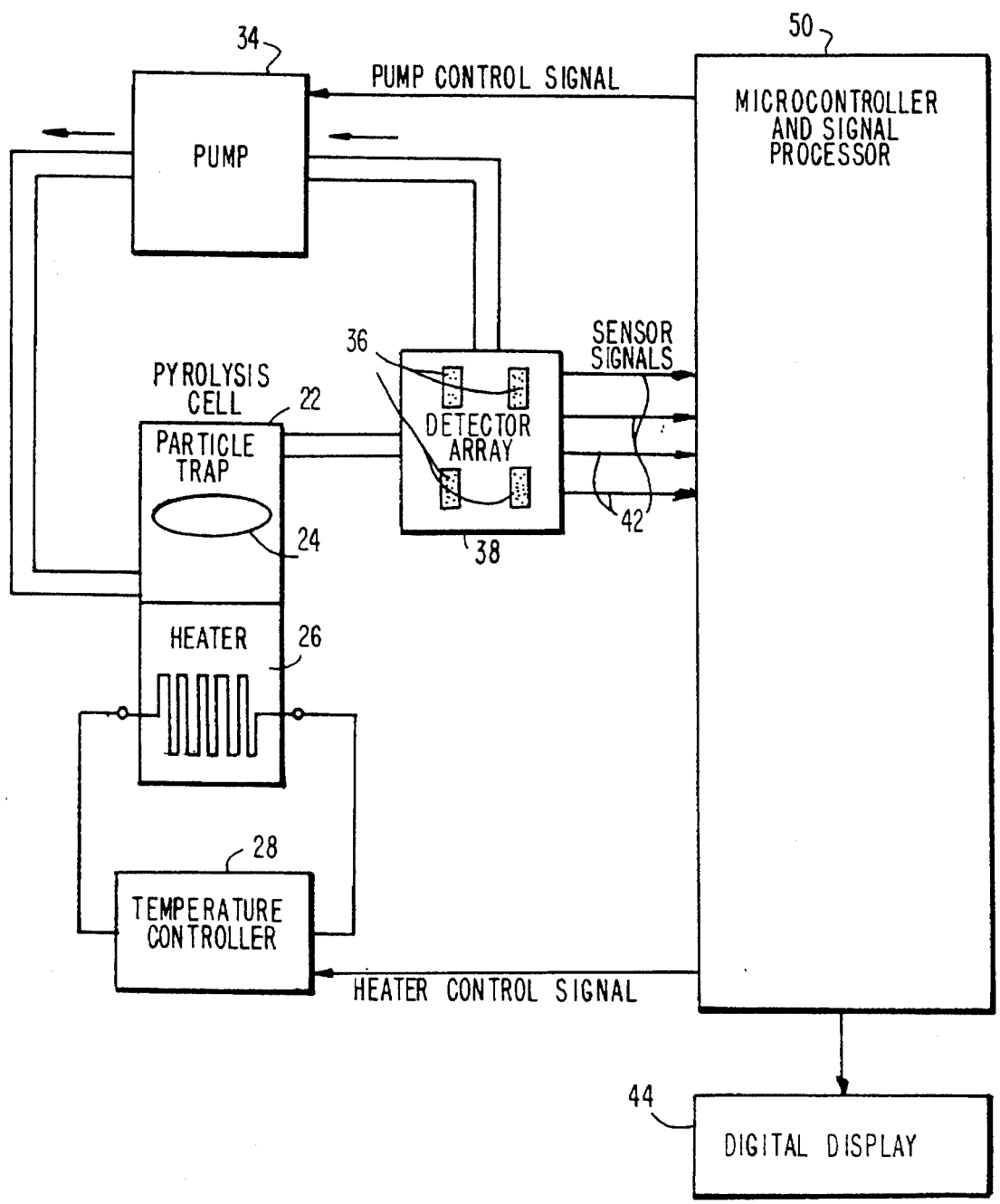
FIG. 2 is a schematic diagram of apparatus for pyrolyzing a chemical substance, and identifying pyrolysis products thereof, as aforesaid.

The invention can be further understood with respect to FIGS. 1 and 2. These Figures illustrate a system which includes a pyrolysis means, a detection means, an extraction means, a comparator means and a control means.

Referring to FIGS. 1 and 2, a sample made up primarily of dust and aerosols, which possibly contains an illicit chemical substance such as cocaine hydrochloride, is drawn through inlet port 18 into trap 24 (comprising, e.g., a bed of glass wool) by the action of a high flow rate air pump 34 through conduit 20. The trap is located in pyrolysis cell 22 (i.e., a pyrolysis chamber). Once the sample has been collected and concentrated in trap 24, the pyrolysis cell 22 is purged through a tube 20 with a reference atmosphere that can be ambient air or ambient air that has been cleaned and dried, effected again by the pull of pump 34. The pyrolysis cell is vented through line 16 and outlet port 14. This reference atmosphere is also drawn from the pyrolysis cell 22 into the detection chamber 38 by the pull of pump 40 through conduit 44. The detection chamber holds the detector equipment, which comprises an array of four sorbent-coated SAW resonators 36 (in which five sensors—four sorbent-coated and one uncoated—are used) coated with various materials, each one of the resonators 36 known to adsorb one or more pyrolysis products of the chemical substance. The signals resulting from the SAW array's contact with the references atmosphere are initially recorded prior to pyrolyzing the chemical substance. The signals are transmitted to unit 50, which is a microcontroller that controls all instrument functions (e.g., the pyrolyer—using temperature control unit 28—and pumps), as well as processes and analyzes data received from the sensors 38. Once this is done, the pyrolysis cell 22 is heated using a resistance heater 26 to a temperature of about 200° C. When a chemical substance of interest is present in the sample, gaseous pyrolysis products are generated as a result of the substance's pyrolysis. For example, if cocaine hydrochloride is present in the filter 24, then it will be pyrolyzed to yield such gaseous materials as benzoic acid, methyl amine and a variety of cycloheptatriene compounds. The pyrolysis products are then drawn into the SAW array. As a result of interaction between the various pyrolysis products and the sorbent-coated sensors, signals 42 are generated and transmitted to unit 50.

The microcontroller of unit 50 powered by 12 volt (D.C.) battery 48 compares the signals generated by the SAW array after and before pyrolysis, and based on differences between them, produces a "fingerprint pattern", the intensity of which is related to the amount of chemical substance present. Unit 50 incorporates three small circuit cards consisting of a RF card, a sensor interface card and a basic CPU card, which were designed and fabricated to perform system and analysis functions. The circuit cards, each 4½ inches square, were stacked on top of each other to conserve space in the module.

The "RF Card" contained Radio Frequency (RF) amplifiers to excite the SAW oscillators and RF mixers and analog voltage comparators to produce the digital frequency differences between the active SAW sensors and the reference device.

The "Sensor Interface Card" is responsible for power regulation, frequency counting, and control of external pumps and alarms.

The "Basic CPU Card" contains the system microcomputer (i.e., an Intel 8052AH processor with a resident BASIC interpreter) along with 8K of random access memory, 8K of EPROM program memory, 48 digital I/O lines and an RS232C serial port. The system software controls the operation of the air pumps, valves, pyrolyzer, and the collection and processing of sensor data.

The relative intensities of the signals 42 from each of the four SAW sensors 36 constitute the fingerprint that can be used in conjunction with a computerized pattern recognition algorithm to confirm the presence of the chemical substance.

A digital read-out 46 enhances the user friendliness of the system.

Figure 3A:
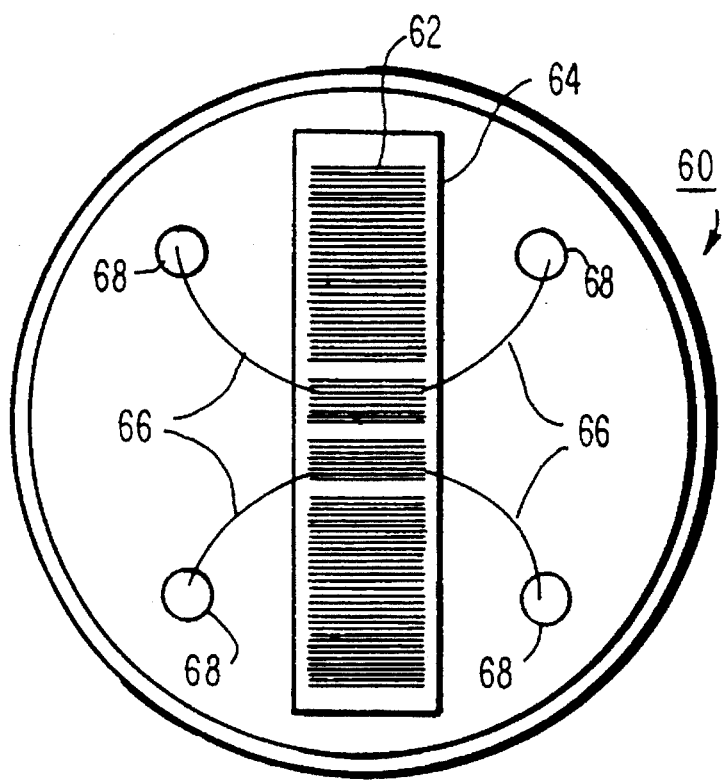
FIG. 3A is an enlarged top view drawing of SAW sensor 36 as described in this invention.
Figure 3B:
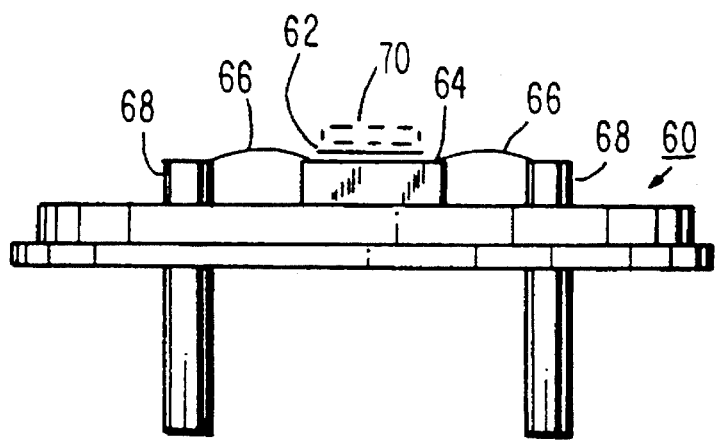
FIG. 3B is an enlarged side view drawing of such sensor.

As shown in FIGS. 3A and 3B, each SAW sensor 60 is typically a nominally 250 MHz resonator sensor 62 fabricated on ST quartz 64. The active sensor is approximately 0.08 cm2, exhibiting a short term noise around ±2 Hz RMS, and a detection limit in the range of 0.006 nanogram. Each sensor is bonded with conductive epoxy to a conventional 0.5 inch TO-8 style header and joined by electrical connector 66 to the four gold-plated pins 68 thereof. Each of the sensors is typically coated with a polymer 70 (shown in phantom in FIG. 3B) to make the sensors vapor sensitive. The fifth SAW resonator shown in FIG. 2 is uncoated, sealed and used as a temperature and pressure reference for the four active sensors. When exposed to chemical vapors, the polymer coatings absorb vapor in proportion to their concentration in air, thereby changing the mass loading on the SAW sensor and giving a corresponding change in frequency. Thus, the frequency of the SAW device is directly related to vapor concentrations. By using four different polymers, each having a different affinity for organic vapors, simple sensor response patterns are developed that serve as "fingerprints" for vapors to which the sensor array is exposed. When combined with a pattern recognition algorithm, the array thereby provides selective detection of target vapors (i.e., gaseous pyrolysis products).

Figure 4:
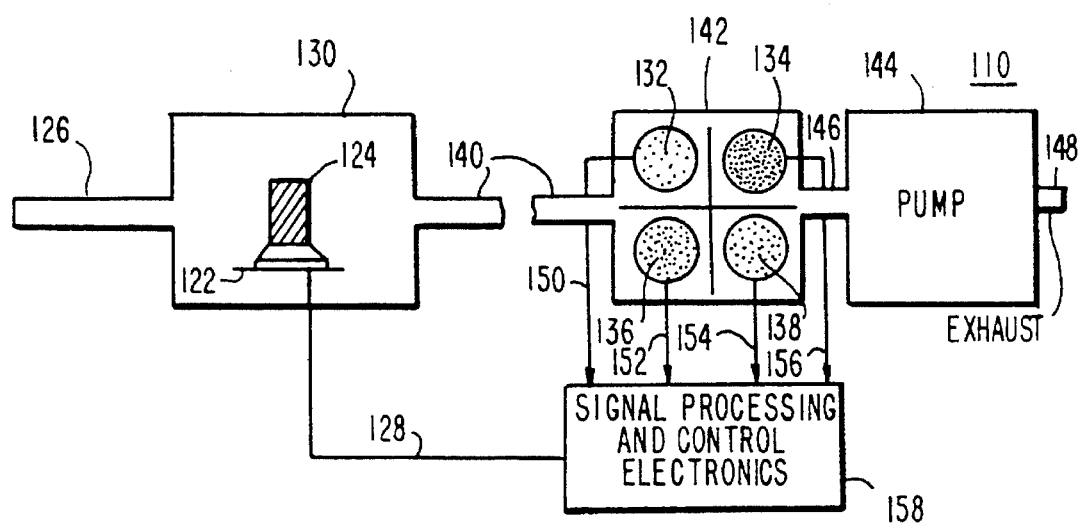
FIG. 4 is a schematic view of combined pyrolysis and sensor components in accordance with the invention.

FIG. 4 shows pyrolysis equipment and associated sensor subassembly 110 for concentrating, detecting and identifying any gaseous pyrolysis products generated by pyrolyzing the non-volatile chemical substance of interest which may be present. A compartment defined by walls 130 contains resistance heating element 122, and trap 124 comprising a bed of glass wool. Ambient air, possibly containing dust and aerosol particles to be investigated is introduced into the pyrolysis compartment through line 126. The particles are trapped by glass wool 124, and subjected to a temperature of about 200° C. by actuating heating element 122. In the event the chemical substance of interest (in this case cocaine hydrochloride) is present, it is pyrolyzed and the gaseous products then extracted from the pyrolysis compartment through line 140, and introduced into a sensor compartment defined by walls 142. The sensors contained in the sensor compartment are piezoelectric sensor components which are coated with sorbent materials; the sorbent: materials used in beds 132, 134, 136 and 138 are chosen so that the selectivity of each to a gaseous pyrolysis product of interest which may be present differs from the selectivity to such products of the other three sorbent materials. The sensor compartment in which the array of sensors 132, 134, 136 and 138 is housed communicates with pump 144 via tube 146. Pump 144 operates to draw ambient air into the system through inlet tube 126 and expels air which has already passed through the system at exhaust 148. As can be seen from lines 150, 152, 154 and 156, the above-discussed sensors are connected by appropriate circuitry to a signal processing and control electronics unit 158. Unit 158 includes a pattern recognition processor which employs a pattern recognition algorithm to detect and identify any gaseous pyrolysis products which are in the gaseous materials drawn into the system at tube 140. As is further shown, power is supplied to resistance heater 122 by unit 158 through electrical connection 128.

In operation, ambient air is drawn through tube 126 (by the action of pump 144) into the pyrolysis compartment. The ambient air passes through glass wool 124. After a brief sampling period (e.g., one minute) during which the ambient air passes through glass wool 124 and dust and aerosol particles are removed, sensors 132, 134, 136 and 138—which have interacted with the gaseous materials in the pyrolysis compartment prior to pyrolysis—are activated and the signals generated the thereby processed by unit 158. Then, the glass wool trap is heated (e.g., for a period of 30 seconds) by operation of the resistance heater 122. The heating causes pyrolysis of any chemical substance of interest in the collected dust and aerosol sample. Any pyrolysis products are then combined with ambient air flow passed through tube 140 and contacted with the array of sensors 132, 134, 136 and 138, and sorbed by the sorbent materials of the aforementioned sensors. Flow of this air past the array of sensors causes those sensors to output a characteristic pattern of signals which is relayed to and processed by unit 158. The sequence can be repeated until several spectra of output signals from the sensor array housed in the detection compartment have been provided to unit 158 for analysis. In each case, air passing through compartment 142 is conducted via duct 146 through pump 144 and exhausted at tube 148. Thus, with the present invention substantial difficulties encountered in conventional techniques are eliminated. Additionally, substantial advantages which are not necessarily achieved with conventional technology are attendant upon practice of the invention.

The following examples are presented to illustrate but not to limit the subject invention.

EXAMPLE 1

Feasibility of Low Temperature Cocaine Hydrochloride Pyrolysis

A Hewlett Packard 5890 Series II gas chromatograph with a flame ionization detector was chosen as the reference instrument. Chromatographic conditions were established for the resolution of methyl benzoate and benzoic acid, two of the anticipated characteristic low temperature pyrolysis products of cocaine hydrochloride. The chromatographic conditions selected were: 120° C., 175 kPa column head pressure, 35 in.×0.125 in. OVA101/(80/100 mesh) Chromosorb column. Methyl benzoate exhibited a retention time of about 1.7 minutes, and a sensitivity of 3200 (±10%) area units/nanogram when injected in acetone solution. Benzoic acid exhibited a retention time of about 2.4 minutes and a sensitivity of 900 area units/nanogram when injected in acetone.

A 200 microgram sample of cocaine hydrochloride was placed in a 31 ml glass vial. The vial was closed with a Teflon-lined silicone rubber septum, through which a syringe needle was placed to serve as a pressure vent. The vial was heated for 10 minutes at 230° C. Then 2 ml of the vapor within the vial was injected into the gas chromatograph (GC) for analysis. The methyl benzoate peak had an area of approximately 60,000, corresponding to about 30 ng of the ester. The benzoic acid peaks therefore varied from about 2,000,000 to 4,000,000, corresponding to 2.2 to 4.4 micrograms of benzoic acid. Based on these data, and a maximum yield of one mole of benzoic acid per mole of cocaine hydrochloride, the efficiency of the low temperature thermal decomposition (pyrolysis) of cocaine hydrochloride was calculated as 60%.

EXAMPLE 2

Detection of Methyl Benzoate and Benzoic Acid

SAW array sensitivity to pure methyl benzoate and benzoic acid was determined by syringe injection of vapors into the SAW array. Absolute vapor amounts were determined by correlation with parallel GC analysis. Samples were heated in closed, vented vials in an oven at 230° C. for a minimum of 10 minutes prior to syringe withdrawal of a vapor sample. The sample was taken through a septum with a glass syringe and immediately injected through a septum into a short Teflon tube leading to the SAW array. Results of one such test are shown in Table 1.

TABLE 1

Results of injecting pure methyl benzoate or benzoic acid into the SAW sensor array

| Sample Conc. (ug/cc) | Injection Volume | Responses of coated SAW Devices (kHz) | | | |
|---|---|---|---|---|---|
| | | SAW #1 | SAW #2 | SAW #3 | SAW #4 |
| Methyl Benzoate | | | | | |
| 0.24 | 5 cc | 1.0 | −0.2 | −0.05 | 0.65 |
| 32.5 | 2 cc | 0.7 | −0.1 | 0.0 | 5.6 |
| (second injection 2 cc injection) | | | | | |
| 32.5 | 2 cc | 3.4 | −0.2 | 0.0 | 5.6 |
| 35.0 | 8 cc | 4.5 | 0.15 | 0.75 | 9.3 |
| Benzoic Acid | | | | | |
| 14.7 | 8 cc | 12.5 | 15.5 | 12.0 | 24.4 |
| 0.65 | 8 cc | 6.3 | 5.2 | 1.8 | 10.4 |
| 0.46 | 8 cc | 0.4 | 0.6 | 0.45 | 0.95 |

The results shown in Table 1 again demonstrate the difficulty in transferring the vapor phase compounds from a heated vial to the SAW sensor package. Variations in the time required for sample withdrawal and insertion by syringe are believed to be the main cause for the scatter in the data. These tests were repeated many times over many days with the results of Table 1 being qualitatively typical. It should be noted that these preliminary results can not be extrapolated to lower concentrations due to nonlinearity induced by the relatively high sample loss by absorption at the lower concentrations.

Figure 5:
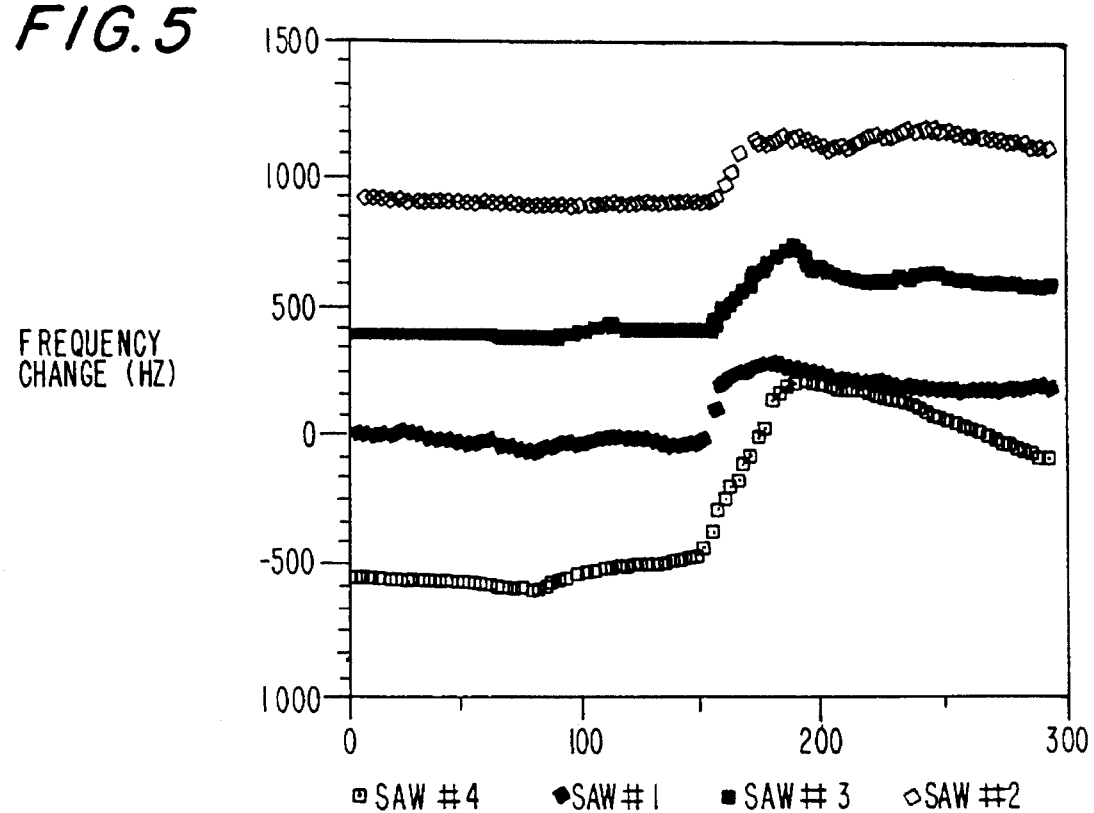
FIG. 5 is a curve showing a typical kinetic response of the sensors when a sample is introduced into the SAW array in a simulation of the invention.

Even with the scatter in data, the results show that each of the SAW sensors responds with good sensitivity to the typical pyrolysis products of cocaine hydrochloride. A 1 KHz signal corresponds to approximately a 550:1 signal to noise ratio, which means that if the system response were linear, the vapors could easily be detected well into the low nanogram range. Different sensor responses to each of these vapors are important as they are the basis for developing pattern recognition algorithms for the detection and identification of cocaine hydrochloride from its pyrolysis outgassing "signature". The plots of frequency change (in signals from the sensors) v. time depicted in FIG. 5 show that the SAW devices respond very rapidly to the presence of the typical pyrolysis (and in this simulation to the presence of benzoic acid; sample injected at t=150 seconds).

EXAMPLE 3

Detection of Cocaine Hydrochloride Pyrolysis Products

Figure 6:
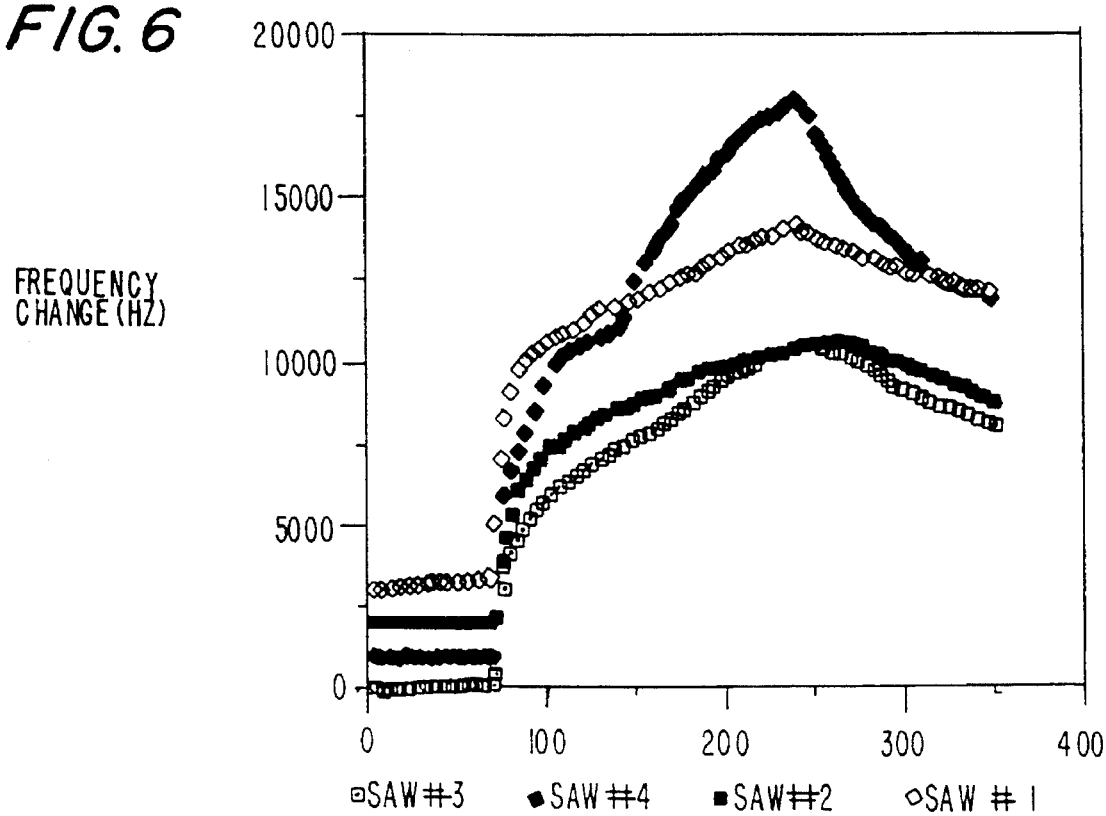
FIG. 6 is a curve showing typical kinetic response of the sensors when a sample is introduced into the SAW array in a simulation of the invention.

SAW array sensitivity to cocaine hydrochloride pyrolysate was determined by heating cocaine hydrochloride in an oven then injecting the resulting vapors directly into the SAW sensor package. 200 ug samples of cocaine hydrochloride were heated in a sealed, vented 31 ml glass vial at 230° C. for a minimum of 10 minutes prior to withdrawal of the vapor. The sample was immediately injected into a short Teflon tube leading to the SAW array. The benzoic acid concentration in the pyrolysate was determined by correlation with parallel GC analysis. Typical results of these tests are shown in Table 2. FIG. 6 shows typical plots of frequency change (in signals from the sensors) v. time depicting sensor response to vapor from heated cocaine hydrochloride (sample introduced at t=75 seconds).

TABLE 2

Results of SAW Sensor Array to Cocaine Hydrochloride Pyrolysis Vapors Benzoic Acid

| Sample Conc. (ng/cc) | Injection Volume | Responses of coated SAW Devices (kHz) | | | |
|---|---|---|---|---|---|
| | | SAW #1 | SAW #2 | SAW #3 | SAW #4 |
| 756 | 8 cc | 10.6 | 8.2 | 11.2 | 17.6 |
| 683 | 8 cc | 6.0 | 2.8 | 2.2 | 6.6 |
| 680 | 8 cc | 2.4 | 1.2 | 1.2 | 6.0 |

Again, rapid absorption and recrystallization of benzoic acid on the cooler walls of the syringe and transfer lines causes large differences in signal magnitude from one run to the next. This was noticeable in both the SAW and GC measurements. Even with this scatter, the results clearly demonstrate that each of the SAW sensors responds to the actual pyrolysis products of cocaine hydrochloride. The different magnitude of signal response for the different sensors is also desirable for purposes of detection and identification. FIG. 6 demonstrates once again that the SAW sensors respond rapidly to the presence of the pyrolysis vapors. Although not shown in the figures, it should be pointed out the SAW sensors had a relatively long cleardown time, which may also contribute to the measurement variability.

EXAMPLE 4

Test of Pyrolyzer/Sensor Array System

Figure 7:
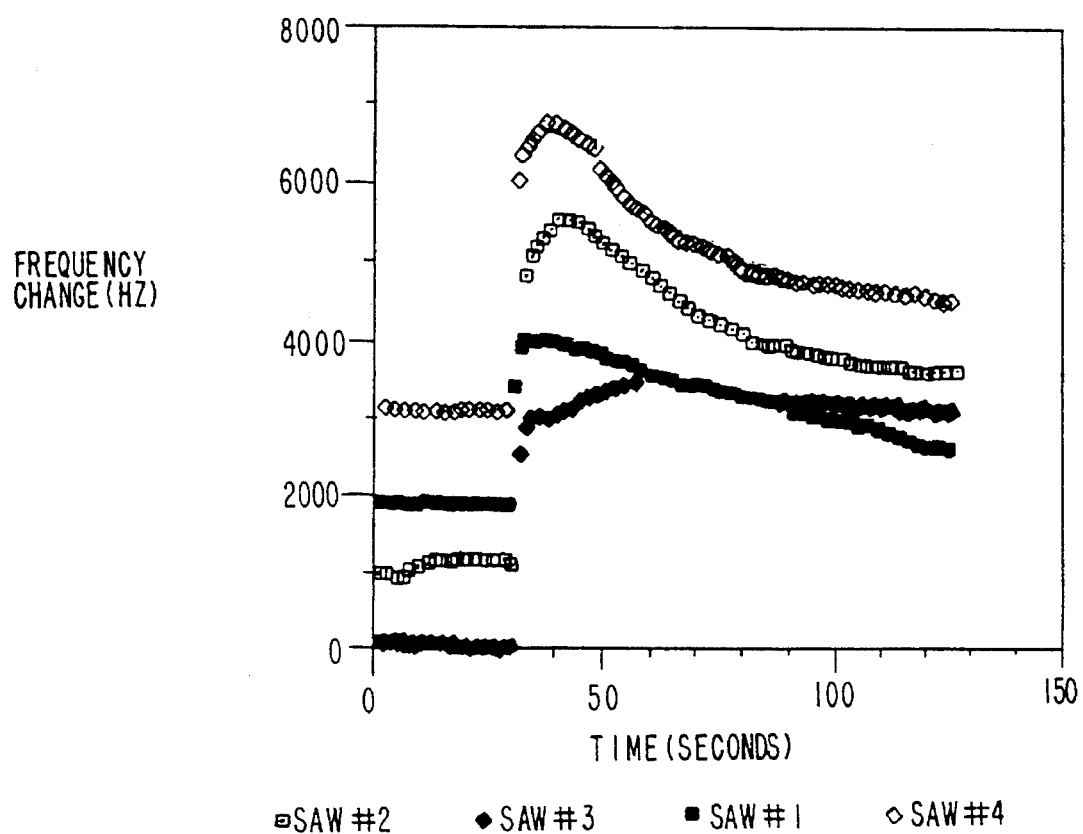
FIG. 7 is curve showing typical kinetic response of the sensors when a sample is heated to pyrolyze cocaine hydrochloride in accordance with the invention.

A test of the complete system consisted of placing a solid sample within the pyrolyzer, heating it, and transferring the vapors to the SAW sensor array. FIG. 7 shows plots of frequency change (in the signals from the sensors) v. time depicting the SAW sensor array response to vapor from pyrolyzed cocaine hydrochloride (sample injected at t=25 seconds).

For these tests 50 to 100 ug samples of cocaine hydrochloride were placed inside a glass capillary tube. The tube was inserted into the pyrolyzer and heated to 230° C. over a 90 second interval, with at least 30 seconds at the maximum temperature. The sample pump was turned on to draw vapor continuously at 0.40 liters per minute from the pyrolyzer to the sensor array package. Pyrolysis vapors from 100 ug samples gave large signals (±10 KHz) when contacted with "clean" SAW sensors, i.e., sensors that have been adequately purged. For vapor exposures made in rapid succession, the SAW sensor responses fell off as the vapor loading in the coatings increased. The sensors themselves recovered their sensitivity in about 10–20 minute with room temperature clean air purging.

As expected, GC analysis of the cocaine hydrochloride pyrolysate vapors showed several peaks in addition to that due to benzoic acid, although benzoic acid was a primary constituent. The presence of additional compounds in the vapor was reflected in the SAW array "patterns", which were not identical to that for pure benzoic acid.

The terms and expressions which have been employed herein are used as terms of description and not of limitation, and there is no intention in the use of such terms and expressions to exclude any equivalents of the features described or of portions thereof, its being recognized that various modifications are possible within the scope of the invention.

What is claimed is:

1. A method for determining the amount of a non-volatile chemical substance of interest present in a sample, which comprises the steps of:

(a) introducing said sample into a pyrolysis zone;

(b) subjecting said sample to an elevated temperature no more than 300° C. such that any sample is pyrolyzed to yield a pyrolysis product;

(c) extracting an amount of atmospheric gaseous material from said pyrolysis zone, and introducing said amount of gaseous material into a detection zone, where said amount is contacted with a sensing apparatus which selectively senses the presence of a product of the pyrolysis of said chemical substance and produces a sensor pattern signal representative of the results of such sensing; and (d) analyzing the signal produced due to sensing of said atmospheric gaseous materials to indicate the presence and amount of said chemical substance of interest in the sample.

2. A method as defined in claim 1, wherein said sample is collected in a trapping filter.

3. A method as defined in claim 2, wherein said trapping filter comprises porous teflon or porous glass fiber.

4. A method as defined in claim 2, wherein said trapping filter is inserted into said pyrolysis zone at room temperature.

5. A method as defined in claim 1, which further comprises purging said pyrolysis zone with ambient air prior to introduction of said sample into said pyrolysis zone.

6. A method as defined in claim 1, wherein said pyrolysis takes place at a temperature up to and including 230° C.

7. A method as defined in claim 1, wherein said chemical substance of interest is cocaine hydrochloride or heroin.

8. A method as defined in claim 1, which comprises contacting said amount of atmospheric gaseous material with an array of sensors, the selectivity of each sensor to said pyrolysis product differing from such selectivity of any other said sensor.

9. A method as defined in claim 8, wherein each said sensor comprises a sorbent coating, thereby to sorb in each said coating a pyrolysis product for which the sorbent coating is selective.

10. A method as defined in claim 9, wherein said sorbent coating absorbs said pyrolysis product.

11. A method as defined in claim 8, wherein said sensors comprise a piezoelectric sensor, an electrochemical cell or a metal oxide semiconductor.

12. A method as defined in claim 11, wherein said piezoelectric sensor is a surface acoustic wave sensor.

13. A method for determining the amount of a non-volatile chemical substance of interest present in a sample, which comprises the steps of:

(a) introducing said sample into a pyrolysis zone;

(b) extracting a first amount of atmospheric gaseous material from said zone;

(c) introducing said first amount into a detection zone, where said first amount is contacted with a sensing apparatus which selectively senses the presence of a product of the pyrolysis of said chemical substance and produced a signal representative of the results of such sensing;

(d) subjecting said sample to an elevated temperature less than 300° C. such that any of said chemical substance of interest present in the sample is pyrolyzed to yield a pyrolysis product;

(e) extracting a second amount of atmospheric gaseous material from said pyrolysis zone, and introducing said second amount of gaseous material into a detection zone, where said second amount is contacted with a sensing apparatus, such that when said pyrolysis product is present it is selectively sensed and said apparatus produces a signal representative of the results of such sensing; and (f) comparing the respective signals produced due to sensing of said first and second amounts of atmospherics gaseous material as an indication of the amount of said chemical substance of interest present in the sample.

14. A method as defined in claim 13, wherein the step of comparing said signals includes analyzing said signals by use of a computerized pattern recognition algorithm.

15. A method as defined in claim 13, wherein said computerized pattern recognition algorithm analyzes a fingerprint pattern produced by said detection means.

* * * * *